(12) United States Patent
Kang et al.

(10) Patent No.: US 10,151,712 B2
(45) Date of Patent: Dec. 11, 2018

(54) VEHICLE-CARRIED QUICK INSPECTION SYSTEM

(71) Applicants: Tsinghua University, Haidian District, Beijing (CN); Nuctech Company Limited, Haidian District, Beijing (CN)

(72) Inventors: Kejun Kang, Beijing (CN); Xuejing Yang, Beijing (CN); Shangmin Sun, Beijing (CN); Yu Hu, Beijing (CN); Jingyu Gu, Beijing (CN); Weifeng Yu, Beijing (CN); Ke Li, Beijing (CN); Lei Liu, Beijing (CN); Youai Yu, Beijing (CN)

(73) Assignees: Tsunghua University, Beijing (CN); Nuctech Company Limited, Beijing (CN)

( * ) Notice: Subject to any disclaimer, the term of this patent is extended or adjusted under 35 U.S.C. 154(b) by 123 days.

(21) Appl. No.: 14/982,374

(22) Filed: Dec. 29, 2015

(65) Prior Publication Data

US 2016/0187526 A1 Jun. 30, 2016

(30) Foreign Application Priority Data

Dec. 29, 2014 (CN) .......................... 2014 1 0837355

(51) Int. Cl.
*H05G 1/46* (2006.01)
*G01N 23/10* (2018.01)
(Continued)

(52) U.S. Cl.
CPC ........... *G01N 23/10* (2013.01); *B62D 65/005* (2013.01); *H05G 1/46* (2013.01); *G01N 23/18* (2013.01);
(Continued)

(58) Field of Classification Search
CPC .. H05G 1/00; H05G 1/02; H05G 1/08; H05G 1/26; H05G 1/30; H05G 1/46; H05G 1/56;
(Continued)

(56) References Cited

U.S. PATENT DOCUMENTS

2004/0017887 A1* 1/2004 Le ........................... G01N 23/04
378/57
2009/0270168 A1 10/2009 Shi et al.
(Continued)

FOREIGN PATENT DOCUMENTS

CN 103026214 A 4/2013
CN 103675930 A 3/2014
(Continued)

OTHER PUBLICATIONS

Office Action for corresponding Russian Patent Application No. 2015156106/11(086509) dated Dec. 16, 2016.
(Continued)

*Primary Examiner* — Anastasia Midkiff
(74) *Attorney, Agent, or Firm* — Knobbe, Martens, Olson & Bear, LLP (57) ABSTRACT

The present disclosure provides a vehicle-carried inspection system, including a radiation source and a detector, the radiation source and the detector being arranged to form an inspection passage. The inspection system further includes a controller configured to control the radiation source so that a first dose of radiation which is safe to a driver is radiated from the radiation source when the driver's cab of the inspected vehicle passes through a ray beam, and control the radiation source so that the dose of radiation of the radiation source becomes a working dose of radiation larger than the first dose of radiation when the other subsequent portions of the inspected vehicle pass through the ray beam.

18 Claims, 4 Drawing Sheets

(51) Int. Cl.
  *G01N 23/18* (2018.01)
  *B62D 65/00* (2006.01)
  *G01V 5/00* (2006.01)
(52) U.S. Cl.
  CPC .............. *G01N 2201/0216* (2013.01); *G01N 2223/301* (2013.01); *G01N 2223/306* (2013.01); *G01N 2223/308* (2013.01); *G01V 5/0016* (2013.01); *G01V 5/0066* (2013.01); *G05B 2219/37125* (2013.01); *G05B 2219/40544* (2013.01)
(58) Field of Classification Search
  CPC ...... G01N 23/00; G01N 23/02; G01N 23/025; G01N 23/04; G01N 23/05; G01N 23/06; G01N 23/08; G01N 23/083; G01N 23/087; G01N 23/09; G01N 23/10; G01N 23/16; G01N 23/18; G01N 2291/00; G01N 2291/01; G01N 2291/011; G01N 2291/0289; G01N 2291/048; G01N 2291/26; G01N 2291/269; G01N 2291/2698; G01N 2223/00; G01N 2223/03; G01N 2223/04; G01N 2223/10; G01N 2223/101; G01N 2223/1013; G01N 2223/1016; G01N 2223/30; G01N 2223/301; G01N 2223/306; G01N 2223/308; G01N 2223/321; G01N 2223/33; G01N 2223/3307; G01N 2223/3308; G01N 2223/40; G01N 2223/631; G01N 2223/643; G01N 2201/00; G01N 2201/02; G01N 2201/021; G01N 2201/0216; G01N 2201/024; G01N 2201/025; G01N 2201/0438; G01N 2201/0484; G01N 2201/10; G01N 2201/11; B62D 65/00; B62D 65/005; G05B 2219/37125; G05B 2219/40572; G05B 2219/21003; G05B 2219/37103; G05B 2219/40544; G05B 2219/39259; G06K 7/10415; G06K 7/10425; G06K 7/10435; G06K 9/00362; G08C 21/00
  See application file for complete search history.

(56) References Cited

U.S. PATENT DOCUMENTS

| | | |
|---|---|---|
| 2009/0271068 A1 | 10/2009 | Shi et al. |
| 2011/0038453 A1 | 2/2011 | Morton et al. |
| 2011/0186739 A1 | 8/2011 | Foland et al. |
| 2013/0039462 A1 | 2/2013 | Morton |
| 2014/0016756 A1* | 1/2014 | Kotowski .............. G01N 23/04 378/147 |
| 2014/0121097 A1 | 5/2014 | Phillips et al. |
| 2014/0192958 A1 | 7/2014 | Dinca et al. |
| 2015/0139386 A1* | 5/2015 | Star-Lack ............ G01V 5/0016 378/57 |
| 2015/0219785 A1* | 8/2015 | Tudor ................. G01V 5/0016 378/57 |

FOREIGN PATENT DOCUMENTS

| | | |
|---|---|---|
| CN | 103984035 A | 8/2014 |
| CN | 204287511 U | 4/2015 |
| WO | 2009088706 A2 | 7/2009 |
| WO | 2011106745 A1 | 9/2011 |
| WO | 2014121097 A1 | 8/2014 |

OTHER PUBLICATIONS

Office Action for corresponding CN Application No. 2017050901548560 dated May 12, 2017.
Search Report dated May 9, 2016 in corresponding EP Application No. 15200666.4.
International Search Report and Written Opinion issued by the Intellectual Property Office of Singapore in application No. 10201510547X dated Oct. 24, 2017.
Second Office Action dated Sep. 4, 2017 issued by the European Patent Office for the parallel European patent application No. 15200666.4.
Second Search Report and Written Opinion dated Jul. 30, 2018 for Singapore Application No. 10201510547X in 10 pages.

* cited by examiner

VEHICLE-CARRIED QUICK INSPECTION SYSTEM

CROSS-REFERENCE TO RELATED APPLICATION

This application claims the benefit of the Chinese Patent Application No. 201410837355.6 filed on Dec. 29, 2014 in the State Intellectual Property Office of China, the whole disclosure of which is incorporated herein by reference.

BACKGROUND OF THE INVENTION

Field of the Invention

Embodiments of the present disclosure relate to the field of security inspection, and particularly, to a vehicle-carried inspection system.

Description of the Related Art

Radiation imaging inspection technologies are necessary security inspection means for customhouses, subways, civil aviation airports and railway systems. During inspection under an existing vehicle-carried inspection system, an inspected vehicle needs to stop at a designated position, and all persons including a driver on the vehicle get off the vehicle and go away from a scanning region, then the inspection system moves on its own at a speed so as to complete inspection on the inspected vehicle; in this scanning mode, a scanning speed is generally in a range of 0.2~0.6 m/s, and the maximum limit of inspection efficiency is 30 vehicles/hours in theory. There is a need to provide a vehicle-carried inspection system, which can not only keep motility and flexibility characteristics of a vehicle-carried inspection system, but also increase the inspection rate so as to improve the inspection efficiency.

SUMMARY OF THE INVENTION

An object of the present disclosure is to provide a vehicle-carried inspection system, which not only has motility and flexibility characteristics, but also enables efficient inspection.

According to one aspect of the present disclosure, there is provided a vehicle-carried inspection system, for being mounted on a vehicle, the inspection system comprising: an X-ray source capable of providing an adjustable radiation dose and configured to radiate X-rays of a desired dose to irradiate the inspected vehicle; a detector configured to be located at a position opposite to the X-ray source and to receive information about X-rays passing through the inspected vehicle, the X-ray source and the detector being arranged on opposite sides of an inspection passage through which the inspected vehicle moves during inspection; the vehicle-carried inspection system further comprises a controller configured to control the X-ray source to radiate different portions of the inspected vehicle with different doses.

According to one aspect of the present disclosure, the vehicle-carried inspection system further comprises a foldable rotation mount, on which the detector is arranged. In a road travelling state, the foldable rotation mount is foldable onto or within the vehicle provided with the vehicle-carried inspection system; in an inspection working state, the foldable rotation mount is moved to be in a direction transverse to the inspection passage and is unfolded to form the inspection passage.

According to one aspect of the present disclosure, the vehicle-carried inspection system further comprises one or more first sensors configured to sense a vehicle adjacent thereto so as to send a signal to the vehicle-carried inspection system for being ready for inspection.

According to one aspect of the present disclosure, the vehicle-carried inspection system further comprises a plurality of second sensor configured to sense a position of the inspected vehicle relative to the X-ray source and to transmit information about the position of the inspected vehicle to the controller.

According to one aspect of the present disclosure, the plurality of second sensors are arranged and configured to measure a relative speed between the vehicle-carried inspection system and the inspected vehicle.

According to one aspect of the present disclosure, the controller is further configured to, according to a sensing result from the second sensors, control the X-ray source so that the X-ray radiation dose is reduced or the radiation is stopped so as to avoid radiation damage to a human body when a driver's cab of the inspected vehicle passes through the X-ray beam. In one embodiment, the controller is further configured to, according to a sensing result from the second sensors, control the X-ray source to irradiate a designated portion of the inspected vehicle with a first dose of radiation or to stop radiation onto the designated portion, and to irradiate other portions of the inspected vehicle with a working radiation dose of radiation larger than the first dose of radiation when the other portions pass through the X-ray beam.

According to one aspect of the present disclosure, the controller is arranged to perform inspection, in conjunction with the relative speed between the vehicle-carried inspection system and the inspected vehicle measured by the plurality of second sensors, so as to form an X-ray image.

According to one aspect of the present disclosure, the controller is arranged to perform inspection, in conjunction with the relative speed between the vehicle-carried inspection system and the inspected vehicle measured by the plurality of second sensors, so as to alarm and interrupt the inspection when a relative moving speed of the inspected vehicle exceeds a maximum limit value or is below a minimum limit value.

According to one aspect of the present disclosure, the vehicle-carried inspection system further comprises an indicator light device configured to display an indication to allow the inspected vehicle to pass through the inspection system when the inspection system is ready for inspection, otherwise to display a prohibition indication.

According to one aspect of the present disclosure, the first sensor is a geomagnetic sensor, a microwave sensor, or a laser sensor.

According to one aspect of the present disclosure, the ray source is a γ ray source or a neutron ray source.

According to one aspect of the present disclosure, there is provided an inspection vehicle, comprising the vehicle-carried inspection system as described above.

With the vehicle-carried inspection system according to embodiment of the present disclosure, a mobile and fully automated security inspection system is obtained and inspection can be achieved, while protecting the driver from being damaged from X-ray radiation. Compared to fixed inspection systems or mobile inspection systems in prior arts, the vehicle-carried inspection system according to embodiments of the present disclosure can provide more convenient inspection.

DETAINED DESCRIPTION OF PREFERRED EMBODIMENTS OF THE INVENTION

A vehicle-carried inspection system 11 according to embodiments of the present disclosure, which is set up on a vehicle 1, will be described below with reference to FIGS. 1-4.

The vehicle-carried inspection system comprises an X-ray radiation source, for example, an X-ray accelerator 12, capable of providing an adjustable dose of radiation and arranged on the vehicle 1 provided with the vehicle-carried inspection system 11. Preferably, the X-ray accelerator 12 is mounted on the tail portion of the vehicle 1 provided with the vehicle-carried inspection system. It will be appreciated that in other embodiments, the X-ray accelerator 12 is mounted at other positions on the vehicle 1 provided with the vehicle-carried inspection system. The X-ray accelerator 12 can radiate X-rays with a working dose of radiation when inspecting an object, for example, container/goods in a container vehicle. However, when the head portion or other designated portion, that is, a portion where a person is located, of the container vehicle, passes in the vicinity of the X-ray accelerator 12, the X-ray accelerator 12 stops radiating X-rays, or the dose from the X-ray accelerator 12 is adjusted to a dose which improves radiation safety to the person. The dose of X-rays may be set by those skilled in the art as desired. The vehicle-carried inspection system may be operated by an operator to implement inspection.

Figure 1:
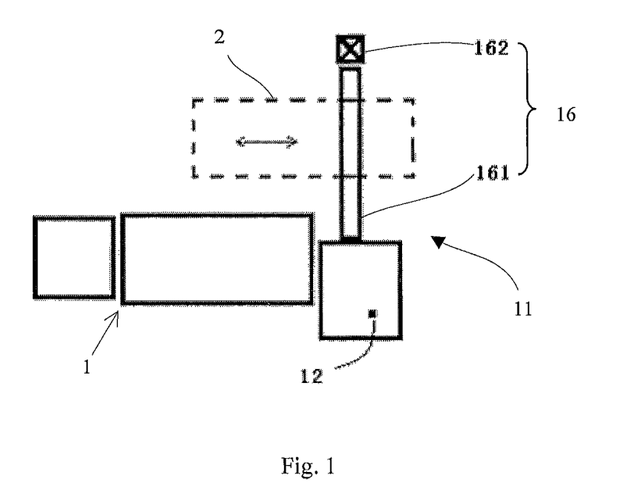
FIG. 1 is a top view of a vehicle-carried inspection system according to an embodiment of the present disclosure.
Figure 2:
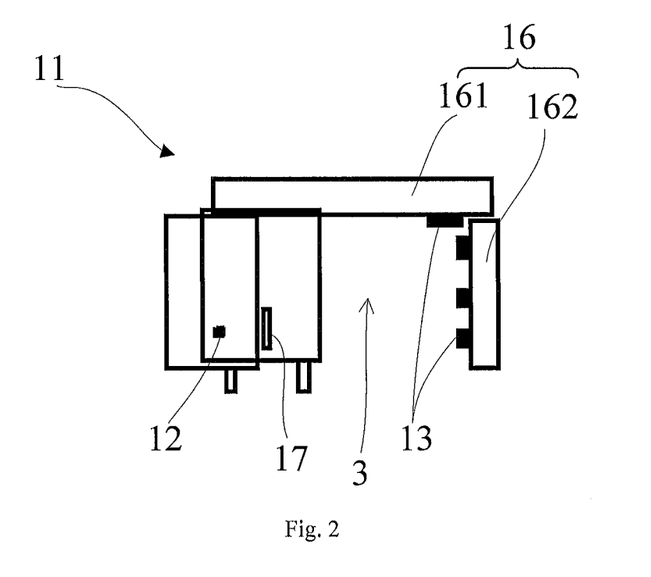
FIG. 2 is a rear view of a vehicle-carried inspection system according to an embodiment of the present disclosure.
Figure 3:
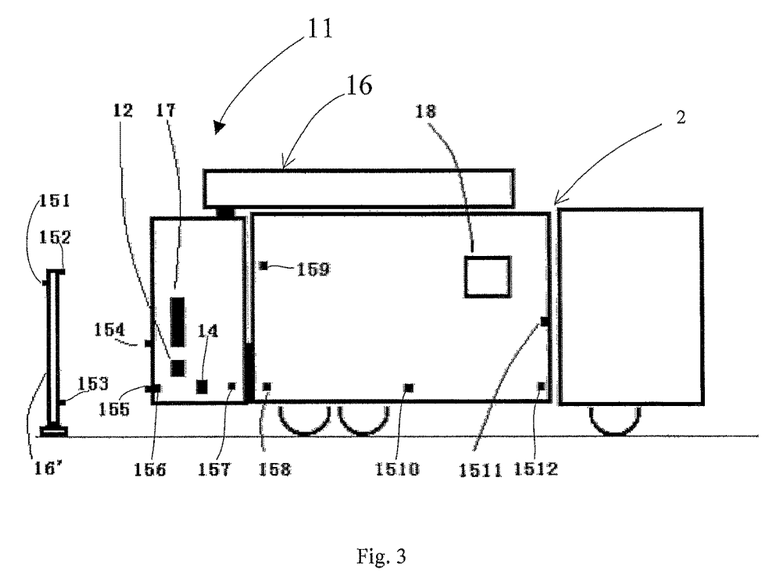
FIG. 3 is a side view of a vehicle-carried inspection system according to an embodiment of the present disclosure, showing arrangement of a plurality of sensor.
Figure 4:
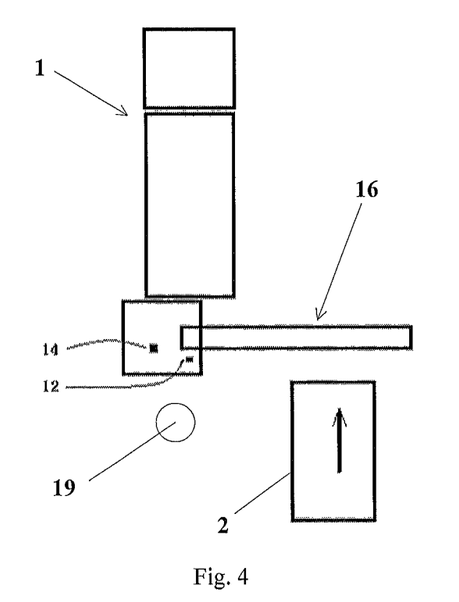
FIG. 4 shows a vehicle-carried inspection system which is inspecting a container vehicle 2.

In an embodiment, the vehicle-carried inspection system 11 further comprises a detector 13 and a mount 16 on which the detector 13 is arranged. The mount 16 comprises a first mount arm 161 and a second mount arm 162. The mount 16 is preferably connected to and supported on the tail portion of the vehicle 1. More preferably, the mount 16 is pivotally supported on the tail portion of the vehicle 1. When the vehicle 1 travels, for example, towards a destination, the mount 16 is folded and placed on the top of the vehicle 1, or is folded within the compartment of the vehicle 1, as shown in FIG. 3. When the vehicle 1 stops and implements inspection on, for example, the container vehicle 2, the mount 16 is pivoted, so that the first mount arm 161 extends in a transverse direction of the vehicle body of the vehicle 1 provided with the vehicle-carried inspection system 11 and the second mount arm 162 is unfolded so as to extend in a vertical direction, thereby forming or define an inspection passage 3, in conjunction with the vehicle body, as shown in FIGS. 1, 2 and 4. Preferably, electric devices such as a motor, joints and hydraulic driving devices are provided to achieve automatic pivoting and unfolding operation of the mount 16, thereby further simplifying inspection operations and improving inspection efficiency. In this case, the detector 13 mounted on the mount 16 is arranged on a side of the inspection passage 3 opposite to the X-ray accelerator 12, that is, the X-ray accelerator 12 and the detector 13 are arranged on opposite sides of the inspection passage 3. In some embodiments, the detector 13 comprises a plurality of detectors 13 arranged on the second mount arm 162, the detectors 13 are also arranged on the first mount arm. The detector(s) is arranged on a side opposite to the X-ray accelerator 12 and is configured to collect X-rays emitted from the X-ray source and transmitted through the container vehicle, so that information about the container vehicle can be obtained by analyzing collected X-ray radiation signals, for example, so as to determine whether or not there is any contraband in the container.

In an embodiment, a collimator 17 is provided in front of the X-ray accelerator 12, and a position and a size of the collimator 17 is set by those skilled in the art as required.

Compared to an inspection station fixed in position, the above arrangement enables mobility of the X-ray inspection system 11, providing great convenience in practical use; further, the foldable and extendable mount 16 is configured so that inspection operation is simple, that is, the inspection passage can be constructed quickly in field to be ready to inspect a mobile object such as a vehicle, and the mount can be folded and stored quickly, for leaving the field.

In order to implement security inspection, the vehicle-carried inspection system according to the present disclosure further comprises a controller 18 configured to control the X-ray accelerator 12 to radiate an appropriate radiation dose as required. For example, during a period when the container vehicle 2 passes through the inspection passage 3, the head portion of the container vehicle 2 firstly enters the inspection passage, and the controller 18 controls the X-ray accelerator 12 to reduce radiation dose so as to avoid damage to the driver when the head portion passes through an X-ray radiation region. After the head portion or a designated portion of the vehicle passes through the X-ray radiation region, the container enters the X-ray radiation region, at this time, the controller 18 controls the X-ray accelerator 12 to increase the radiation dose, that is, enter into a working dose inspection state.

According to embodiments of the present disclosure, the controller 18 is provided to control the radiation dose of the X-ray accelerator 12, thereby avoiding damages to persons, which is important in safety in actual applications.

Different regions or portions of the inspected vehicle may be identified through human eyes, or may be identified by various kinds of sensors, such as a photoelectric switch, an ultrasonic switch, light curtain, a laser sensor, or a ground sensing coil.

According to another embodiment of the present disclosure, the vehicle-carried inspection system further comprises at least one first sensor 14 and a plurality of second sensors, for quickly providing inspection.

In an embodiment, the first sensor is a geomagnetic sensor 14, and is mounted in the vicinity of the X-ray accelerator 12. The geomagnetic sensor 14 may sense the vehicle based on a change in ambient magnetic field. For example, when no container vehicle is approaching, the geomagnetic sensor 14 senses a background magnetic field which is stored by the controller 18. When a container vehicle 2 is approaching, there is a change in magnetic field, which is sensed by the geomagnetic sensor 14, thereby it can be determined that the container vehicle 2 is approaching. Of course, in other embodiments, a microwave or laser sensor is used to achieve the function of sensing the vehicle.

Once the geomagnetic sensor 14 senses that the container vehicle 2 is approaching, the vehicle-carried inspection system enters into a state ready for inspection, thereby enabling automation operation of the vehicle-carried inspection system. For example, the geomagnetic sensor 14 may transmit the sensed signal to the controller 18, and controller 18 actuates the inspection system to enter into the inspection state.

In an example, the second sensor is a photosensor. When the container vehicle 2 is approaching, light (for example, radiation light from the inspection system) reflected by the container vehicle 2 is sensed by the photosensor, thus, a position of the vehicle can be determined through the photosensor. In an embodiment of the present disclosure, the number of the second sensors is eight; for example, second sensors 155, 156, 157, 158, 159, 1510, 1511 and 1512 are provided. The photosensors 155, 156 are arranged on a side surface of the vehicle 1, are spaced apart from each other by a fixed distance, and are located at different heights, thereby portions of the vehicle body of the container vehicle 2 having different heights can be sensed. When the head portion of the container vehicle 2 begins to enter the inspection passage, the photosensors 155, 156 sense the head portion and transmit a signal indicative of the head portion to the controller 18, then the controller 18 controls the X-ray accelerator 12 to reduce radiation dose or to stop radiation; when the container portion of the container vehicle 2 begins to enter the X-ray radiation region, the photosensors 157, 158 and 159 sense and judge that the container portion enter the X-ray radiation region, and the controller 18, after receiving signals from the sensors, controls the X-ray accelerator 12 to increase radiation dose, that is, enter into a working dose inspection state.

In a further embodiment of the present disclosure, the number of the second sensors is twelve, and these photosensors 151-1512 are arranged on one side surface of the vehicle 1, spaced apart from one another, and located at different heights, so that portions of the vehicle body of the container vehicle 2 having different heights can be sensed. When the head portion of the container vehicle 2 enters the inspection passage in a direction from the head portion to the tail portion of the vehicle 1, the photosensors 157, 158, 159 sense the head portion of the container vehicle 2 and transmit a signal indicative of the head portion of the container vehicle 2 to the controller 18, and the controller 18 controls the X-ray accelerator 12 to reduce radiation dose or to stop radiation; after the head portion of the container vehicle passes through the sensors 151, 152 and 153, the container portion of the container vehicle begins to enter the X-ray radiation region, then the photosensors 151, 152 and 153, in conjunction with the sensors 154-159, sense that the container portion enters the X-ray radiation region, and the controller 18, after receiving signals from the sensors, controls the X-ray accelerator 12 to increase radiation dose, that is, enter into a working dose inspection state. When the sensors 151, 152 and 153 sense that the tail portion of the container vehicle has passed therethrough, the controller 18 receives signals from the sensors and controls the X-ray accelerator to stop radiation so as to finish inspection.

In an embodiment, the second sensors are arranged so that there are a plurality of the second sensors within a local region. These photosensor are spaced apart from one another by a known distance and configured to measure a position of one same portion of a mobile object, so that a time interval by which mobile object 2 passing through these spaced photosensors can be sensed through these photosensor, and thus a relative movement speed of the mobile object 2 can be calculated. The techniques of sensing a mobile object by using photosensors so as to determine the position of the mobile object and to measure a speed of the mobile object are well known to those skilled in the art. For example, the second sensor is a camera (CCD), and the speed of the mobile object can be determined through cooperation of the sensor and a reference object such as a grating. If it is known that a person is locating at a position on the mobile object 2, the second sensor may transmit a signal to the controller 18, so that radiation is reduced or stopped for the region where the person is locating.

It would be advantageous to arrange a plurality of sensors on the side surface of the vehicle 1, preferably, over the side surface in a longitudinal direction of the vehicle body, so that a distance between the container vehicle 2 and the vehicle 1 can be sensed. When the container vehicle 2 deviates from the inspection passage, for example, the container vehicle 2 is too close to the vehicle-carried inspection system and there is a possibility of collision, the vehicle-carried inspection system may alarm to warn the driver to correct the vehicle body.

It is preferable that the container vehicle 2 passes through the inspection passage in a uniform rectilinear motion during inspection, and the movement speed of the container vehicle 2 is in an appropriate range, which can be determined according to parameters of the X-ray inspection system in practice. When it is sensed that the relative speed of the container vehicle 2 is greater than an upper speed limit of the range or less than a lower speed limit of the range, the vehicle-carried inspection system will give an alarm and the inspection is interrupted.

Thus, the vehicle-carried inspection system according to embodiments of the present disclosure is integrated into a whole, and compared to existing inspection systems, has a better mobility, enables automated and inspection operations by means of the controller 18 as well as the first sensor 14 and the second sensor, and can expedite inspection rate while ensuing safety of persons, thereby having important applications in practice.

According to embodiments of the present disclosure, when the vehicle provided with the vehicle-carried inspection system reaches a field such as a port, the mount 16 is driven to pivot and be unfolded so as to form an inspection passage. When the container vehicle 2 approaches the vehicle-carried inspection system, the geomagnetic sensor senses a change in magnetic field, and transmits a signal to the controller 18, thereby the controller 18 starts the inspection system. When the head portion of the container vehicle 2 begins to enter the inspection passage, the photosensors sense that the vehicle head portion enters an X-ray radiation region and transmit signals indicative of the position and the speed of the vehicle head portion to the controller 18, and the controller 18 controls the X-ray accelerator 12 to stop working or reduce dose of radiation to a safe dose. The driver drives the vehicle to travel at a constant speed, and when sensing that the container portion enters the X-ray radiation region, the photosensor transmits a signal to the controller 18, then the controller 18 controls the X-ray accelerator 12 to increase radiation dose. The controller 18 receives a signal indicative X-rays transmitted through the container and detected by the detector 13, and displays information about scanned objects within the container vehicle on a display in combination with the shape and the speed of the container.

Thus, when the vehicle carrying the vehicle-carried inspection system reaches an inspection field, inspection operation can be launched within several minutes, and the container vehicle 2 only needs to passes through the inspection passage at a constant speed in an appropriate range, thereby completing inspection; further, the whole inspection operation is fully automated, without any additional operations by the operator. For example, a container vehicle 2 having a length of 18 meters passes through the inspection passage at a speed of 2 m/s, the inspection of the container vehicle can be completed within 10 seconds.

The container vehicle 2 may enter the inspection passage from the tail portion of the vehicle 1 provided with the vehicle-carried inspection system, or may enter the inspection passage from the head portion of the vehicle 1.

When the container vehicle 2 enters the inspection passage from the head portion of the vehicle 1, it is required to provide an additional mount 16', which is preferably mounted on the vehicle 1, and on which photosensors 151, 152 and 153 are mounted and configured to transmit signals to the controller 18 when the head portion of the container vehicle passes the additional mount 16', so that the controller 18 actuates the X-ray accelerator 12 to increase radiation dose, thereby the vehicle-carried inspection system enters into a working dose inspection state.

In an embodiment, the vehicle-carried inspection system further comprises an indication device. For example, the vehicle-carried inspection system comprises an indicator light device 19 (see FIG. 4). When the container vehicle 2 moves at a constant speed to approach the vehicle-carried inspection system, the indicator light device of the vehicle-carried inspection system displays a green indicator light, for example. In this case, the container vehicle 2 continues to passes through the inspection passage 3. When the container vehicle 2 is being located within the inspection passage, the indicator light device displays a red color, so that a container vehicle waiting behind is prohibited from entering the inspection passage. An alarm device may also be provided to give an alarm indication when the inspection is interrupted.

Compared to conventional combined mobile inspection systems, with the technique solutions provided according to the embodiments of the present disclosure, a transfer from one field to another field can be achieved, that is, no particular field is needed, and an occupying area is small; the security inspection vehicle can be driven away after inspection, without obstructing normal use of a road. For example, if it is required to quickly perform a security inspection within such a region as small as possible or within a temporary region, the technique solutions provided according to the embodiments of the present disclosure can be applied. Further, according to the embodiments of the present disclosure, the security inspection vehicle is driven to a section of an existing road through which a container vehicle will necessarily pass, and the driver only needs to drive the vehicle through the section of the road at a normal speed, so that the inspection is completed quickly with a high efficiency, without providing a separate security inspection field. The security inspection vehicle may stop at a parking area or garage when not working, occupying a small area; when the security inspection vehicle needs to be maintained, it is driven to a designated repair shop for convenient maintenance.

Having further described the objectives, technical solutions and advantageous effects of the present disclosure in detail in the above exemplary embodiments, it will be appreciated that the above described contents are only preferred embodiments of the present disclosure, and are not intended to limit the present disclosure. All changes, alternatives or modifications which are made the principles and spirit of the present disclosure should fall within the scopes of the present invention. Thus, the scopes of the present invention should be limited only by the claims.

What is claimed is:

1. A vehicle-carried inspection system, adapted to be arranged on a carrying vehicle and comprising:
    a foldable arm mount provided on the carrying vehicle and configured to be folded onto or within the carrying vehicle in a transportation state and to be unfolded to span over an inspected vehicle in a working state so as to form an inspection passage through which the inspected vehicle passes during inspection;
    an X-ray radiation source capable of providing an adjustable dose of radiation, said X-ray radiation source being provided on the carrying vehicle in both the transportation state and the working state and configured to radiate X-rays of a desired dose of radiation to irradiate the inspected vehicle;
    a detector provided on the foldable arm mount and configured to be located at a position opposite to the X-ray radiation source, the detector being further configured to receive information about X-rays passing through the inspected vehicle in the working state, wherein, in said working state, the X-ray radiation source and the detector are arranged on opposite sides of the inspection passage for the inspected vehicle and the inspected vehicle passes through the inspection passage and the detector is located at a farther position from the carrying vehicle than the X-ray radiation source;
    a first sensor configured to sense a vehicle adjacent thereto so as to send a signal to the vehicle-carried inspection system to be ready for inspection; and
    a controller configured to control the X-ray radiation source to irradiate different portions of the inspected vehicle with different doses of radiation,
    wherein the vehicle-carried inspection system further comprises an additional mount and photosensors mounted on the additional mount, the photosensors being configured to transmit signals to the controller when a head portion of the inspected vehicle passes the additional mount in a direction from a head portion to a tail portion of the carrying vehicle, so that the controller actuates the X-ray source to increase radiation dose, thereby the vehicle-carried inspection system enters into a working dose inspection state.

2. The vehicle-carried inspection system according to claim 1, further comprising a plurality of second sensors configured to sense a position of the inspected vehicle relative to the X-ray radiation source and to transmit information about the position of the inspected vehicle to the controller.

3. The vehicle-carried inspection system according to claim 2, wherein the plurality of second sensors are arranged and configured to measure a relative speed between the vehicle-carried inspection system and the inspected vehicle.

4. The vehicle-carried inspection system according to claim 2, wherein the controller is further configured to, according to a sensing result from the second sensors, control the X-ray radiation source so that the dose of radiation is reduced or the radiation is stopped so as to avoid radiation damage to a human body when a driver's cab of the inspected vehicle passes through the X-rays.

5. The vehicle-carried inspection system according to claim 2, wherein the controller is further configured to, according to a sensing result from the second sensors, control the X-ray radiation source to irradiate a designated portion of the inspected vehicle with a first dose of radiation or to stop radiation onto the designated portion, and to irradiate other portions of the inspected vehicle with a working dose of radiation larger than the first dose of radiation when the other portions pass through the X-rays.

6. The vehicle-carried inspection system according to claim 3, wherein the controller is further configured to perform inspection, in conjunction with the relative speed between the vehicle-carried inspection system and the inspected vehicle measured by the plurality of second sensors, so as to form an ray image.

7. The vehicle-carried inspection system according to claim 3, wherein the controller is further configured to perform inspection, in conjunction with the relative speed between the vehicle-carried inspection system and the inspected vehicle measured by the plurality of second sensors, so as to alarm and interrupt the inspection when a relative moving speed of the inspected vehicle exceeds a maximum limit value or is below a minimum limit value.

8. The vehicle-carried inspection system according to claim 1, further comprising an indicator light device configured to display an indication to allow the inspected vehicle to pass through the inspection system when the inspection system is ready for inspection, otherwise to display a prohibition indication.

9. The vehicle-carried inspection system according to claim 1, wherein the first sensor is a geomagnetic sensor, a microwave sensor, or a laser sensor.

10. An inspection vehicle, comprising the vehicle-carried inspection system according to claim 1.

11. An inspection vehicle, comprising the vehicle-carried inspection system of claim 1.

12. An inspection vehicle, comprising the vehicle-carried inspection system of claim 2.

13. An inspection vehicle, comprising the vehicle-carried inspection system of claim 3.

14. An inspection vehicle, comprising the vehicle-carried inspection system of claim 4.

15. An inspection vehicle, comprising the vehicle-carried inspection system of claim 5.

16. An inspection vehicle, comprising the vehicle-carried inspection system of claim 6.

17. An inspection vehicle, comprising the vehicle-carried inspection system of claim 7.

18. An inspection method, comprising performing an inspection on a moving object by using the vehicle-carried inspection system according to claim 1.

* * * * *